United States Patent [19]

McCollester

[11] Patent Number: 4,720,386

[45] Date of Patent: Jan. 19, 1988

[54] VACCINE AND METHOD FOR IMMUNOTHERAPY OF NEOPLASTIC DISEASE

[76] Inventor: Duncan L. McCollester, Beech La., Tarrytown, N.Y. 10591

[21] Appl. No.: 307,191

[22] Filed: Sep. 30, 1981

Related U.S. Application Data

[63] Continuation of Ser. No. 127,041, Mar. 4, 1980, abandoned, which is a continuation-in-part of Ser. No. 744,601, Nov. 24, 1976, abandoned.

[51] Int. Cl.$^4$ .................... A61K 39/00; A61K 31/74
[52] U.S. Cl. ........................................ 424/88; 424/78
[58] Field of Search .................................. 424/78, 88

[56] References Cited

PUBLICATIONS

Spencer, Cancer Research, Part 2, vol. 25, No. 4, May, 1975, p. 963 (4715).

Dyer, An Index of Tumor Chemotherapy, NIH, 1949, pp. 10 and 30.

*Primary Examiner*—Jerome D. Goldberg
*Attorney, Agent, or Firm*—Pennie & Edmonds

[57] ABSTRACT

A novel vaccine for use in the immunotherapy of neoplastic disease is prepared by a procedure wherein cancerous tissue is surgically removed from a patient to be treated and the tissue is disaggregated into its component cells which are then suspended in water and subjected to hydrodynamic turbulence sufficient to disrupt the cells. The "cell disruption material", possessing cancer-specific antigen, and which comprises cell surface membranes and in some cases also intracellular particles, is mixed with a source of maganous ion (e.g., manganese hydrogen phosphate) and, optionally, a triphosphate gel (e.g., manganese tri-phosphate) to produce the vaccine. When inoculated into the patient, the vaccine promotes regression of the cancer through stimulation of the patient's immune response.

12 Claims, No Drawings

VACCINE AND METHOD FOR IMMUNOTHERAPY OF NEOPLASTIC DISEASE

REFERENCE TO RELATED APPLICATION

This is a continuation of application Ser. No. 127,041, filed Mar. 4, 1980, now abandoned, which is a continuation-in-part of application Ser. No. 744,601, filed Nov. 24, 1976 now abandoned

BACKGROUND OF THE INVENTION

This invention relates to the treatment of neoplastic diseases stemming from oncogenesis and collectively known as cancer. More particularly, it relates to a novel vaccine and method for using same in the therapy of malignant neoplasms which afflict mammals, including man, such as sarcomas, the carcinomas, and the hematologic cancers, through the activation or stimulation of the body's immune system to achieve remission and destruction of cancerous tissue. While the term "vaccine" is understood generally to means a bacteriological or viral-derived agent, it is used herein more broadly to encompass substances prepared in accordance with the invention for activating the body's immune response.

The more advanced forms of animal life have the ability to produce substances known as antibodies when exposed to certain agents called antigens. The production of antibodies resulting from the introduction of an antigen into the body is called the "immune response"; its purpose is to protect the body against potentially harmful substances or organisms. A characteristic feature of antibodies is that, for all intents and purposes, they will only combine with the particular antigen which stimulated their production, i.e., a particular antibody will combine only with a specific antigen. Any material may be an antigen. For example, an antigen may be a metal, lipid, protein, carbohydrate or a combination of two or more of these broad classes of materials. Apart from its chemical composition, an antigen can be a whole molecule, a portion of the surface of a molecule or a portion of the surfaces of a group of molecules. On the other hand, all antibodies are individual discrete molecules belonging to a class of proteins known as globulins and as such all antibodies have the same fundamental molecular structure although they do vary in size depending on the molecular weight of their fundamental components.

Although antibodies all have basically the same gross molecular structure, they vary in subtle but distinct ways much as the notches of different keys vary in almost innumerable ways. It is this variation which enables a particular antibody to distinguish between innumerable antigens and to combine only with the specific antigen which stimulated the production of the antibody, much in the same way that a key will fit only its own particular lock. Thus, a particular sequence of "notches" will be found only in a population of antibody molecules which combine with a specific kind of antigen. If the sequence varies only slightly the antibody will not combine with the antigen in question. The current state-of-the-art with respect to what is known about the immune response is exemplified in the article by M. D. Cooper et al. entitled "The Development of the Immune System" appearing in Scientific American, pages 59–72 (November 1972).

Antibodies are either "cellular" or "humoral" depending upon whether they are attached to the surfaces of certain white corpuscles or exist unattached as free individual molecules, respectively. After an antigen is introduced into the body there is a delay of from two to ten days before the appropriate antibodies are manufactured and secreted or discharged into the blood-stream and certain body secretions. (Undoubtedly, antibodies are manufactured more rapidly than this, however, the elapsed time before they can be detected probably reflects the sensitivity of current analytical techniques). The number, type, and combining affinity of the antibodies produced determine the degree or extent of cellular or humoral immunity against the specific antigen in question. As a general rule small antigens stimulate the production of humoral antibodies whereas large antigens, such as those fixed to surfaces or clumps of antigen carriers, lead to the production of cellular antibodies. This distinction is important to an understanding of the role of the immune response in cancer.

The first step in the immune response to a harmful agent is the detection of antigens which are not normally present in the body. The body, of course, contains innumerable antigens of its own. Therefore, the antigens which must be detected are "non-self" or foreign antigens. Detection of foreign antigens is accomplished by constantly monitoring the antigens on all of the cells and molecules within the body. This monitoring function is performed largely by certain kinds of white cells which continuously explore all parts of the body via the circulatory system. When an antigen is found the monitoring cells are "programmed" to respond only if the antigen is foreign to the body, i.e., does not belong there. When a foreign antigen is detected, the monitoring cells responsible for such detection respond by initiating a series of events which ultimately give rise to the production of cellular or humoral antibodies which then combine with the antigen. This antigen-antibody combination usually destroys the harmful biologic effects of the source of the antigen. In this way the body protects itself against toxins and invading microorganisms (viruses, bacteria and parasites). As a general rule, humoral anti-bodies are produced if the antigen is part of a toxin, an individual molecule, virus or bacterium, whereas cellular anti-bodies are produced if the antigen is part of a multi-cellular organism such as a large parasite or a transplant of a foreign tissue. The concept of the "immune response" has been employed in the past for the prevention and treatment of several dreaded infectious diseases, including smallpox and polio. In particular, the prevention or treatment of disease by means of promoting or stimulating the appropriate immune response is known as "immunization" or "immunotherapy", respectively. The general state-of-the-art of immunology which provides the scientific basis for immunotherapy is contained in the following references: M. C. Raff, "Cell-Surface Immunology", *Scientific American*, pages 30–39 (May, 1976); D. T. Rowlands, et al., "Surface Receptors in the Immune Response", *New Eng. J. Med.*, 293 26–32 (1975); and T. Rajan, "The Immune System", *N.Y. State Med. J* 1077–1085 (July, 1976).

In addition to protecting the body against harmful influences invading it from without, the immune response appears for the following reasons to be responsible for protecting the body from certain harmful influences arising from within, namely, the various neoplastic diseases known collectively as "cancer".

First, every cancer which has been adequately tested has been found to possess on the surface of its cells antigens which are foreign to the host. See, for example, the article by R. E. Pollack et al. entitled "The Cell Surface and Malignant Transformation", *Ann. Rev. Med.*, 25, 431–446 (1974). These diseases are characterized by the unremitting multiplication of the cancerous cells without the restraints which govern the "social behavior" of normal cells. As a result, cancer cells push into and invade normal adjacent cells, leading to pain and the destruction of the normal cells. If the normal cells under attack comprise a vital organ, death will often result. In addition, normal cells are selectively adhesive to other normal cells of the same type and through this adherence are able to build up complex organ systems. Cancer cells tend not to adhere to each other, a situation favoring "metastasis" whereby cancer cells break away from the parent cancer tissue and become distributed to other parts of the body where they multiply and invade other normal cells. These resultant metastases often cause pain or death. This abnormal behavior of cancer cells is believed to be due at least in part to cell surface characteristics which are not present in normal cells. The surfaces of normal cells send a signal to the cell nucleus when cell multiplication must cease, as in the repair of a skin wound, a phenomenon known as "contact inhibition". Cancer cell surfaces apparently do not send such signals, as a result of which the cancer cells continue to multiply, piling upon each other and invading normal cells. The factors responsible for these differences between the cell surfaces of normal and cancer cells are believed to comprise, at least in part, the antigens of the cancer which are regarded as "foreign" by the host.

Second, the body possesses the ability to destroy via the immune response a vast number of cells, and indeed, an entire organ. This is seen in the rejection of a kidney or heart transplant. Thus, the destructive capability of the immune response is in some instances immense and, if properly channeled, is presumably capable of destroying newly arising cancers.

Third, the ability of the immune response to destroy large numbers of cells appears on the phylogenetic scale at the same point as cancer. In general terms, when cells multiply there are always a small number thereof which will be abnormal. When the abnormality of one of these cells is manifested in the acquisition of cell surface characteristics which result in unremitting multiplication, invasion of the body, and widespread distribution of daughter cells, the abnormal cell will produce a potentially lethal cancer. As organisms through evolutionary processes have become more complex the likelihood of cancer cells evolving has also increased. Eventually, with increasing complexity of the organism, the frequency of cancer cells appearing became so great that the organism was unable to mature and reproduce. Then in order for evolution to proceed further, a mechanism was needed to protect the organism from the cancer cells constantly appearing within. Evolution apparently developed such a mechanism which is the type of immune response seen in the rejection of a transplanted organ such as a kidney or heart. This type of immune response did not arise to thwart the transplantation surgeon but rather to protect the body against cancer. As mentioned earlier, this type of immune response leads to cellular immunity or cellular immune response as distinct from humoral immunity or humoral immune response.

Finally, the incidence of cancer rises markedly when the cellular immune response is weak, whether the weakness results from inherent defects of the host's immune system or from destruction or suppression of the immune system by drugs, surgery or radiation. This increased incidence of cancer is seen in experimental animals and in humans. In humans, suppression of the immune response by drugs in order to assure the survival of a transplanted kidney has been found to lead to an incidence of cancer 2,000 times greater than that seen in the normal population. This suggests that the degree of suppression necessary to prevent the immune response from destroying the transplanted kidney also weakens the immune response against the abnormal, potentially cancerous cells constantly appearing in the body so that inevitably the frequency of clinical cancer becomes greater. When the immune suppressive therapy is stopped the newly arisen cancer usually disappears.

The relationship between the immune response and cancer leads to the concept of immunologic surveillance, which was initially proposed by Burnet (see F. M. Burnet, "Immunological Surveillance", Pergamon Press, New York 1970 and by Thomas (see L. Thomas in "Cellular and Humoral Aspects of the Hypersensitive State", H. S. Lawrence, ed., p. 259 (Holber, New York 1959)). According to this concept the special white cells, which are responsible for detecting antigens foreign to the host, by constantly monitoring all cells and substances of the body, detect any newly appearing cells having characteristics of cells destined to form cancers. After detection these cells are destroyed by an immune response, and in this manner the body is protected against cancer. Such an immunologic surveillance is performed by the same cellular components responsible for the immune response against, and the rejection of, transplanted organs. Furthermore, the cancer-specific antigens detected by immunologic surveillance are quite similar to the transplantation antigens responsible for the immunologic rejection of transplanted organs. Both cancer-specific and transplantation antigens contain carbohydrates and both are present on the surfaces of their respective cells. Both can stimulate the production of cellular immunity. Indeed, the reason for the existence of immunologic surveillance and its powers were not fully appreciated until its suppression became recognized as essential for the survival of transplanted kidneys. As mentioned earlier, it is the cellular type of immunity which is believed to be evoked against cancer cells which are detected by immunologic surveillance. Likewise, a cellular type of immune response is directed against transplanted organs.

As also mentioned earlier, malignant cells are constantly appearing among the various cell populations within the body. The body's cells must constantly be replenished to make up for losses due to injury or senescence. This is accomplished by cells multiplying when necessary. Each time a cell multiplies there is a finite, albeit slight, chance of an error occurring in its complex machinery for multiplication. Consequently, there is a base level of error which cannot be reduced further, reflecting the extreme complexity of the cellular machinery in operation when a cell multiplies. The incidence of this error, however, can be increased by hereditary factors as well as by environmental factors such as radiation, viruses, and chemicals. While these factors increase the incidence of malignant cells, only a few such cells ever survive immunologic surveillance to multiply and create the disease state of cancer. Evolutionary forces dictate that only those cells that have evolved means for evading immunologic surveillance will develop into cancer. Thus, while the failure of immunologic surveillance may be regarded as the single cause of cancer, there are many factors (viral, carcinogenic, radiative) which increase the frequency with which immunologic surveillance must operate successfully if the host is to be protected against the emergence of cancer. When an error does occur, the two daughter cells produced are often not true replicas of the parent cell. Occasionally the error of replication produces a cell which continues to multiply when the need for multiplication no longer exists. This cell and its daughter cells are now malignant and grow to form a cancer. However, as explained earlier, these malignant cells are usually, recognized by means of their cancer-specific antigens which are foreign to the host and they are normally destroyed by an immune response. The question of how cancers arise despite their possession of antigens foreign to the body and despite immunologic surveillance by the host remains one of the great unsolved problems confronting medical science.

Of the malignant cells constantly developing only a very few survive to become cancers. It is not sufficient for a cell to be abnormal merely with regard to being able to multiply increasingly in order to become a cancer. It must also be abnormal to the extent of acquiring devices or mechanisms capable of enabling it to survive immunologic surveillance. Only a few of these devices are known at present. For instance, cancer cells have long been known to possess on their surfaces proteolytic enzymes potentially capable of producing small fragments of cancer antigens. These small fragments of cancer antigens are more likely to stimulate the production of humoral antibodies than cellular antibodies. In certain instances, although these humoral antibodies do combine with the cancer cells, they do not destroy them. Indeed they appear to coat and protect the cancer cells from destruction by cellular antibodies. In this way, the small fragments of cancer antigens are able to blind the special white cells which look for antigens much as small pieces of tinfoil can blind radar.

Finally, the ability of cancer cells to survive immunologic surveillance may depend upon their ability to secrete substances which inhibit the recruitment of other types of cells when antibodies complex with antigen. Normally, antigen antibody complexes can release substances which attract other types of cells necessary for the rapid immunologic destruction of the cancer cells possessing the antigen. It is conceivable that the participation of these other types of cells could be inhibited by substances secreted by the cancer cells. Thus, a vigorous detection and immunologic destruction of the cancer would not occur.

The treatment of cancer by immunotherapy, pursued earlier in this century with great hope and zeal, began with the discovery that animals could survive and reject lethal transplants of cancer if they were first pre-immunized with small, non-lethal transplants of cancer tissue. However, this approach was unsuccessful in treating human cancer. It was later learned that the success of the animal experiments was solely due to histocompatability differences between the cancer tissue donor and the recipient animals, for immunization against the cancer could be achieved just as readily by immunizing the animal with non-cancerous tissue from the animal supplying the cancer. In other words, there was no evidence that cancer-specific antigens, i.e., antigens unique for the particular cancer, existed. Immunotherapy of cancer, lacking a rationale, fell into disrepute. See W. H. Woglom, *The Cancer Review,* 4, 129–214 (1929). In the 1950's, however, highly inbred mouse strains became available. All members within a given strain possess the same antigens and no others, and it was proved unequivocally that cancer antigens, albeit very weak, do indeed exist. These are antigens which are located on the cancer cell surface, are distinctive for the particular cancer, and are not found in the non-cancerous tissues of the host. Unfortunately, these antigens tend to lose their ability to stimulate a cancer-destructive type of immune response when the cancer dies, making the preparation of an effective conventional vaccine for the immunotherapy of cancer difficult.

Four approaches to cancer immunotherapy utilizing the cancer-specific antigen are currently being evaluated. It is well-recognized that extracts of cancer cells per se have no therapeutic value. However, if cancer cells are treated with the enzyme neuraminidase, which strips off carbohydrate material from the cell surface, the cancer cell antigens in experimental animals appear more capable of stimulating an immune response of value in cancer therapy. Presumably, the action of neuraminidase removes substances masking the cancer antigen. This approach has not been of any demonstrated value in treating cancer in humans. Another approach is to complex the cancer antigens with a strong antigen of another type, the hope being that the immune response elicited against the strong antigens will also produce antibodies specific for the weaker cancer antigens. This approach has been of little success to date, but it may explain some of the small success of another approach to cancer immunotherapy, which utilizes the vaccine of Bacillus Calmet-Guerin (BCG). This vaccine, which normally is injected in order to immunize humans against tuberculosis, also has the property of increasing in a non-specific way the immune response against a variety of antigens when these antigens are administered simultaneously (but not necessarily at the same location) with the BCG vaccine. This approach is being evaluated in various laboratories for use in the treatment of leukemia. It does appear to increase somewhat survival in these diseases. BCG is also being used to treat certain selected cases of malignant melanoma. Some dramatic remissions and even cures have been reported when the BCG is injected directly into the melanoma nodule. Finally, in the fourth approach, there have been a few isolated cases of remission of malignant melanoma following injection of the patient with serum from another patient already in remission from malignant melanoma. Presumably, the donor-patient serum possesses antibodies against the cancer-specific antigens of the patient to be treated.

Other types of immunotherapy include the use of transfer factor or mobilizing factor and of RNA of white cells involved in the immunologic rejection of cancer. While attractive in theory, none of these approaches has proved to be of value in treating experimental or clinical cancer. The general state-of-the-art with respect to cancer immunotherapy is examplified in S. K. Carter, "Immunotherapy of Cancer in Man", *Am. Scientist,* 64, 418–423 (1976); E. C. Holmes, "Immunotherapy of Malignancy in Humans", *J.A.M.A.,* 232(10), 1052–1055 (1975); M. R. Hilleman, "Approaches to Control of Cancer by Immunologic Procedures", *Comparative Leukemia Research,* pages 105–130 (Pergamon Press 1966); and L. J. Old, "Cancer Immunology", *Scientific American,* pages 62–79 (May, 1977).

In summary, immunotherapy is regarded today as a secondary form of therapy for cancer, useful only as an adjunct to radiation, surgery and chemotherapy, which comprise the primary modalities for the treatment of cancer. It is well recognized that, in theory, immunotherapy holds great promise for the treatment of cancer, but to date this promise remains unfulfilled.

Accordingly, it is an object of the present invention to provide a method for the immunotherapy of neoplastic disease.

Another object is to provide a new vaccine for use in the immunotherapy of neoplastic disease.

These and other objects of the invention, as well as a fuller understanding of the advantages thereof, can be had by reference to the following description and claims.

SUMMARY OF THE INVENTION

The above objects are achieved according to the present invention by means of a novel vaccine comprising a cancer-specific antigen and an adjuvant. The antigen associated with a particular cancer (the "cancer-specific antigen") is first isolated from the patient to be treated, preferably in a more concentrated form than that in which it exists in the tissue from which it was derived. This is accomplished, at least in part, by optimizing the amount of antigen exposed to detection. More specifically, by breaking up a quantity of disaggregated, intact, antigen-containing cancer cells, a greater concentration of cancer-specific antigen can be obtained for detection by the patient's immune system. This autologous antigen is then used to prepare the vaccine which is administered to the patient in a manner which stimulates and amplifies the patient's immune response to the cancer whereupon the autologous cancer tissue remaining within the patient body undergoes remission and is destroyed. The appropriate dosage can be determined by procedures well-known in the medical arts.

Broadly, the vaccine of the present invention comprises a combination of two basic components, namely, a material containing cancer-specific antigen identical to the antigens possessed by the cancer to be treated, and adjuvantal substances. The terms "adjuvant" and "adjuvantal" as used herein refer to substances which increase the immune response of the patient following inoculation with the vaccine. In some instances, technical considerations may preclude the isolation of the cancer-specific antigen for use as a component of the vaccine. In such cases, in situ cancer deposits (e.g., lesions, tumors, nodules) can be injected directly with the adjuvantal substances whereby the in situ cancer serves as the source of tumor-specific antigen, albeit somewhat less desirably than when isolated according to the procedure described below. If technically feasible, the cancer deposits with their injected adjuvantal substances can be also frozen briefly in situ, preferably by local application of liquid nitrogen; however, such an expedient is to be avoided in cases where agglutination is likely to result.

The vaccine of the present invention is produced by first surgically removing an amount of cancerous tissue from a patient to be treated. The amount of tissue required to be isolated will depend upon the nature of the cancer being treated. Generally, at least about 20 milligrams of tissue should be obtained, with between about 1 and 2 grams being preferred. The isolated tissue can be frozen prior to use. The tissue is then desirably broken down into its component cells, in a manner which separates the parenchyma intact from the stroma. This phase of the process, whereby the cancerous tissue is treated so as to remove the stroma and separate the parenchyma into individual cells with intact membranes, is termed "disaggregation". It is carried out at ambient temperature (i.e., 20°–25° C.) for a time sufficient to achieve substantially complete separation of the parenchyma from the stroma The disaggregated cells are next suspended in water at ambient temperature containing between about 100 and 150 mM/l NaCl, preferably about 120 mM/l NaCl, and between about 5 and 15 mM/l ethylenediaminetetraacetic acid ("EDTA"), preferably about 10 mM/l EDTA, at a pH adjusted to between 5.6 and 8.6, and preferably between 7.4 and 8.2, preferably with NaOH and subjected to hydrodynamic turbulence at ambient temperature for a period of time, usually 5–300 seconds, sufficient to disrupt the individual cell structures. The purpose of suspending the disaggregated cells in such an aqueous medium before subjecting them to hydrodynamic turbulence is to facilitate cell disruption by increasing the osmotic pressure across the cell walls. The EDTA is believed to function as a chelating agent and to contribute to the breakdown of the "inter- and intracellular cement," leading to a better break-up of the cells during water extraction.

The resulting "cell disruption material," comprising cell surface membranes and intracellular particles which possess cancer-specific antigens, is desirably treated with aqueous sodium chloride at a concentration and in an amount sufficient to bring the salt concentration in the material to approximately the physiological level, i.e., about 150 millimolar (mM/l). Alkali metal salts such as lithium chloride and sodium acetate are equivalent to sodium chloride for this purpose, although the latter is preferred. The cell disruption material is then mixed with a source of manganous ion ($Mn^{+2}$) and, optionally, a triphosphate gel to produce a vaccine which, when inoculated into the patient, effects regression of the cancer through stimulation of the patient's immune response. The potency of the vaccine may in some cases be preserved or even enhanced by being frozen following its preparation, desirably at a temperature of $-10°$ C. or below and preferably between $-10°$ and $-20°$ C., the frozen vaccine being thawed before use. Such an expedient should not be used, however, in cases where agglutination is likely to occur. Sources of manganous ion suitable for use in the present invention include manganous hydrogen phosphate gel, manganous chloride, manganese carbonate ($MnCO_3$), manganese hydroxide ($Mn(OH)_2$), manganous guanylate and fatty acid salts such as manganous stearate. The triphosphate gel is employed in an amount such that the weight ratio of the cation of the triphosphate to the manganous ion is between 1 and 10. Suitable triphosphate gels can have the following as their polyvalent cationic constituents: zinc, calcium, manganese or aluminum, but not iron or magnesium or other polyvalent cations which could be toxic at the concentration level employed. Preferably, manganese phosphate, $Mn_3(PO_4)_2$ is used as the triphosphate gel.

As indicated above, manganous ion is an essential component of the adjuvantal portion of the vaccine of the present invention. Although manganese appears to be essential for life, relatively little is known about its actual biological function. According to Kolomiitseva, *Gigenie i Sanitaria*, 33, 31–34 (1968), and Antonova, *Vaprosy Pitanilia*, 27, 36–41 (1968), manganese supplementation given in the diet appears to enhance the vigor of the immune response, and dietary manganese appears to be essential for the proper functioning of the immune response. Although copper appears to function in this way, it is not a substitute for manganese in the present invention. Also, it has been reported in *Brit. J. Cancer*, 24, 290–393 (1970) that the use of permanganate lessens pain and discomfort in patients with terminal carcinoma. This observation has not been further pursued nor is its mechanism known. The use of manganous salts in formulating preparations for treating certain types of squamous cell carcinoma in animals known as "Cancer Eye" is described in U.S. Pat. No. 4,053,586.

Radioactive manganese has been used systematically as a technique for the radio-scanning of brain tumors, whose tissues are known to combine more avidly with manganese than does normal brain tissue.

The purpose of the vaccine of the present invention is to enhance the immunogenicity of cancer-specific antigens so as to stimulate the cancer host to develop a strong tumor cell destructive immune response capable of destroying all of the host's cancer cells. Inhibiting this cancer destructive type of immune response is the cancer itself which may be stimulating the host to develop a cancer cell immune protective response. The cancer could achieve this by shedding low molecular weight soluble forms of cancer antigens, thereby stimulating the host to develop humoral antibodies against cancer antigen. These antibodies might then protect the cancer against attack by combining with cancer antigens on the surfaces of living cancer cells thereby covering the cancer cells with a layer of protecting antibody molecules. Alternatively, the production of antibodies alone or the formation of complexes of circulating antibodies with soluble cancer-specific antigens would switch off the posibility of any further immune response or any other type of immune response. Thus, the vaccine competes with the cancer to be treated by stimulating a cancer destructive immune response as opposed to a cancer protecting immune response.

Without wishing to be bound by theory, it is believed that there are several possible mechanisms whereby the manganese constituent of the vaccine of the invention enables the latter to complete successfully against cancer in stimulating the immune response. Thus, manganese could stabilize cancer-specific antigens and prevent them from breaking off the isolated membrane structures to become soluble low molecular weight antigens. Also, the cell membrane agglutinating effects of manganese, by creating large aggregates of cell-specific antigen, would enhance the likelihood of stimulating an immune response of the cellular type as opposed to the humoral type. Further, the stimulation of nucleotide cyclase enzymes by manganese could lead to increased multiplication of the special white cells which initially detect cancer-specific antigens resulting in an enhanced immune response. Finally, manganese, by virtue of its role in the functioning of glycosyl-transferase enzymes, could lead to a closer interaction between the white cells responsible for cancer-specific antigen detection and the membrane attached cancer-specific antigen in the vaccine. This enhanced interaction would increase the ability of the cancer-specific antigen to stimulate an immune response.

While the vaccine without added triphosphate gel is effective in treating experimental tumors in mice when the vaccine is given intraperitoneally, injections of that type in humans are hazardous, the preferred mode of injection being subcutaneous. However, when injected subcutaneously, the vaccine is more effective when it contains triphosphate gel. The fact that a triphosphate gel component enhances the efficacy of the vaccine of the present invention when the latter is injected subcutaneously suggests that some subtle interaction occurs between a triphosphate molecule and the cancer-specific antigen, and/or that such a species is necessary in the subcutaneous environment in order to obtain an effective vaccine. Alternatively, it is possible that the macromolecule mimics internal mucinous macromolecules and provides a physical volume at the injection site wherein cells of immunological surveillance may congregate to detect and react to the cancer-specific antigen.

Description of the Preferred Embodiment

The following example is intended to illustrate, without limitation, the vaccine and method of the present invention as well as the advantages thereof.

In one embodiment of the invention, which is applicable to all tissue types, a portion of the cancer in the patient to be treated is surgically removed with sterile techniques and immediately frozen in a sterile container in sterile 120 millimolar sodium chloride/10 millimolar sodium EDTA. All subsequent steps are performed so as to preserve bacterial sterility. The tissue at a later time is thawed and disaggregated into its component cells and clumps of cells, preferably by means of a device and method of the type disclosed in U.S. Pat. No. 3,941,117, particularly at column 1, line 57 through column 5, line 47, which is incorporated herein by reference. After disaggregation, the cells, which are in the form of a suspension, are subjected to centrifugation at $2000 \times G$ for several minutes and the supernatant liquid is decanted. The pellet volume is now the reference volume for the subsequent steps. Cells already in the free form such as those obtained in blood or other body fluids are similarly centrifuged, their supernatant liquid decanted, and the resulting pellet volume in the reference volume as noted below. No attempts need be made to further purify the cell preparation although it may contain many normal cells of diverse types in addition to cancer cells, since the patient's immune system will produce antibodies only in response to antigens foreign to the host, i.e., the cancer-specific antigen.

After centrifugation, the disaggregated cells are suspended in water by diluting the pellet 50-fold with water and centrifuged for three minutes at $2000 \times G$. The supernatant liquid is carefully decanted or aspirated off and the pellet is diluted 5 to 50-fold with distilled water. The suspension now consists of many swollen and bursting cells and clumps of cells. The suspension is next aspirated and discharged from a 10 to 50 ml syringe 50 times. This procedure subjects the cells to hydrodynamic turbulence which breaks up, i.e., disrupts, most of the cells, whereupon the suspension consists of still intact cell bodies, surface membrane fragments and "ghosts," and numerous intracellular particles. The purpose of cell disruption is thus to preserve and increase the amount of cancer-specific antigens available for detection by immunologic surveillance when the material is injected back into the patient. It also assures destruction of all cells so that live cells are not inoculated back into the patient.

To the cell disruption material is added sufficient 1.0 molar sodium chloride to bring the final sodium chloride concentration to 150 millimolar. This is next mixed with adjuvantal materials, e.g., manganous hydrogen phosphate gel and manganous triphosphate gel, to produce the vaccine which is placed in single dose syringes and frozen and stored until ready for use, at which time the patient is given periodic, e.g. 1 to 3 times per week, subcutaneous injections of the thawed contents of the syringes.

In preparing the manganese hydrogen phosphate gel for use in the present invention, reagent grade materials are used. Thus, to 15 ml of 100 millimolar manganese chloride are added sufficient 100 millimolar disodium hydrogen phosphate to bring the pH to 7.35. Either 100 millimolar sodium carbonate or 100 millimolar sodium hydroxide can also be used to form manganese carbonate and manganese hydroxide gels respectively, in which case the pH is brough to 8 or 9. The turbid suspension is centrifuged for three minutes at 2000×G, decanted, and the pellet suspended in 25 ml of water. Preparation of the gel is now complete. In a similar manner, triphosphate gel can be prepared from manganous chloride and sodium phosphate.

In combining the cell disruption material containing the cancer-specific antigen and the adjuvantal substances to form the vaccine of the invention, the following are combined in the order and amounts indicated.

2.5 ml cell disruption material
0.3 ml 1.0 molar sodium chloride
2.5 ml manganese hydrogen phosphate gel
5.0 ml manganous phosphate gel
5.8 ml 150 millimolar sodium chloride (physiological saline)

In practice, the above concentrations can be varied somewhat without impairment of the vaccine's therapeutic effectiveness. The vaccine, which except for the freezing step is now ready to be administered, can be charged in 1 ml aliquots into 3 ml syringes and kept frozen until needed.

While the foregoing example illustrates the preferred manner of carrying out the present invention, it will be apparent to those skilled in the art that various changes can be made in the practice of the invention without departing from the scope and spirit thereof, as defined in the following claims.

I claim:

1. A vaccine for the immunotherapy of neoplastic disease, said vaccine being produced by:
   (a) obtaining an amount of cancerous tissue from the patient to be treated and suspending said tissue in an aqueous solution of between about 100 and 150 millimolar sodium chloride and between about 5 and 15 millimolar sodium EDTA,
   (b) disaggregating the tissue into its component cells;
   (c) suspending the cells in water;
   (d) subjecting the suspended cells to hydrodynamic turbulence sufficient to disrupt the cells and detach therefrom the cell components possessing cancer-specific antigens; and
   (e) contacting and admixing the cell components obtained in step (d) with a source of manganous ion to form the vaccine.

2. A vaccine produced according to claim 1 wherein:
   the cancerous tissue obtained in step (a) is suspended in an aqueous solution of about 120 millimolar sodium chloride and about 10 millimolar sodium EDTA; and
   the cell components possessing cancer-specific antigen obtained in step (d) comprise cell surface membrances and intracellular particles.

3. A vaccine produced according to claim 2 wherein:
   the cancerous tissue is a sarcoma or carcinoma;
   the water used in step (c) is distilled water;
   the material obtained in step (d) is admixed with aqueous sodium chloride at a concentration and in an amount sufficient to obtain a sodium chloride concentration in said material of about 150 millimolar; and
   the source of manganous ion used in step (e) is selected from the group consisting of manganous hydrogen phosphate gel, manganous chloride, manganous carbonate, manganous hydroxide, manganous quanylate, and manganous fatty acid salts.

4. A vaccine for the immunotherapy of neoplastic disease, said vaccine being produced by:
   (a) obtaining an amount of cancerous tissue from the patient to be treated and suspending said tissue in an aqueous solution of between about 100 and 150 millimolar sodium chloride and between about 5 and 15 millimolar sodium EDTA;
   (b) disaggregating the tissue into its component cells;
   (c) suspending the cells in water;
   (d) subjecting the suspended cells to hydrodynamic turbulence sufficient to disrupt the cells and detach therefrom the cell components possessing cancer-specific antigens; and
   (e) contacting and admixing the cell components obtained in step (d) with a source of manganous ion and a triphosphate gel, said gel having as its cation an ion selected from the group consisting of zinc, calcium, manganese and aluminum to form the vaccine.

5. A vaccine produced according to claim 4 wherein:
   the cancerous tissue obtained in step (a) is suspended in an aqueous solution of about 120 millimolar sodium chloride and about 10 millimolar sodium EDTA; and
   the cell components possessing cancer-specific antigen obtained in step (d) comprises cell surface membranes and intracellular particles.

6. A vaccine produced according to claim 4 wherein:
   the cancerous tissue is a sarcoma or carcinoma;
   the water used in step (c) is distilled water;
   the material obtained in step (d) is admixed with aqueous sodium chloride at a concentration and in an amount sufficient to obtain a sodium chloride concentration in said material of about 150 millimolar;
   the source of manganous ion used in step (e) is selected from the group consisting of manganous hydrogen phosphate gel, manganous chloride, manganous carbonate, manganous hydroxide, manganous guanylate, and manganous fatty acid salts; and
   the triphosphate gel is manganese phosphate.

7. A method for the immunotherapy of neoplastic disease, said method comprising inoculating the patient to be treated with a therapeutically effective amount of a vaccine to activate the patient's immune response against the disease and cause regression of cancerous tissue within the patient, said vaccine being produced by:
   (a) obtaining an amount of cancerous tissue from the patient to be treated and suspending said tissue in an aqueous solution of between 100 and 150 millimolar sodium chloride and between about 5 and 11 millimolar sodium EDTA;

(b) disaggregating the tissue into its component cells;

(c) suspending the cells in water;

(d) subjecting the suspended cells to hydrodynamic turbulence sufficient to disrupt the cells and detach therefrom the cell components possessing cancer-specific antigens; and (e) contacting and admixing the cell components obtained in step (d) with a source of manganous ion to form the vaccine.

8. A method according to claim 7 wherein:

the cancerous tissue obtained in step (a) is suspended in an aqueous solution of about 120 millimolar sodium chloride at about 10 millimolar sodium EDTA;and the cell components possessing cancer-specific antigen obtained in step (d) comprise cell surface membranes and intracellular particles.

9. A method according to claim 8 wherein:

the cancerous tissue is a sarcoma or carcinoma;

the water used in step (c) is distilled water;

the material obtained in step (d) is admixed with aqueous sodium chloride at a concentration and in an amount sufficient to obtain a sodium chloride concentration of about 150 millimolar; and the source of manganous ion used in step (e) is selected from the group consisting of manganous hydrogen phosphate gel, manganous chloride, manganous carbonate, manganous hydroxide, manganous guanylate, and manganous fatty acid salts.

10. A method for the immunotherapy of neoplastic disease, said method comprising inoculating the patient to be treated with a therapeutically effective amount of a vaccine to activate the patient's immune response against the disease and cause regression of the cancerous tissue within the patient, said vaccine being produced by:

(a) obtaining an amount of cancerous tissue from the patient to be treated and suspending said tissue in an aqueous solution of between 100 and 150 millimolar sodium chloride and between about 5 and 15 millimolar sodium EDTA;

(b) disaggregating the tissue into its component cells;

(c) suspending the cells in water;

(d) subjecting the suspended cells to hydrodynamic turbulence sufficient to disrupt the cells and detach therefrom the cell components possessing cancer-specific antigens; and (e) contacting and admixing the cell components obtained in step (d) with a source of manganous ion and a triphosphate gel, said gel having as its cation an ion selected from the group consisting of zinc, calcium, manganese and aluminum to form the vaccine.

11. A method according to claim 10 wherein:

the cancerous tissue obtained in step (a) is suspended in an aqueous solution of about 120 millimolar sodium chloride and about 10 millimolar sodium EDTA; and the cell components possessing cancer-specific antigen obtained in step (d) comprise cell surface membranes and intracellular particles.

12. A method according to claim 11 wherein:

the cancerous tissue is a sarcoma or carcinoma;

the water used in step (c) is distilled water;

the material obtained in step (d) is admixed with aqueous sodium chloride at a concentration and in an amount sufficient to obtain a sodium chloride concentration of about 150 millimolar; and the source of manganous ion used in step (e) is selected from the group consisting of manganous hydrogen phosphate gel, manganous chloride, manganous carbonate, manganous hydroxide, manganous guanylate, and manganous fatty acid salts; and the triphosphate gel is manganous phosphate.

* * * * *